United States Patent
Hodd et al.

(10) Patent No.: US 6,737,496 B2
(45) Date of Patent: May 18, 2004

(54) PHOTOCURABLE SILOXANE POLYMERS

(75) Inventors: Kenneth A. Hodd, Wales (GB); Sverker Norrby, Leek (NL)

(73) Assignee: Pharmacia Groningen BV, Groningen (NL)

( * ) Notice: Subject to any disclaimer, the term of this patent is extended or adjusted under 35 U.S.C. 154(b) by 0 days.

(21) Appl. No.: 10/134,710

(22) Filed: Apr. 29, 2002

(65) Prior Publication Data

US 2003/0088044 A1 May 8, 2003

Related U.S. Application Data

(62) Division of application No. 09/416,773, filed on Oct. 13, 1999, now Pat. No. 6,399,734.
(60) Provisional application No. 60/105,580, filed on Oct. 26, 1998.

(30) Foreign Application Priority Data

Oct. 13, 1998 (SE) ................................. 9803481

(51) Int. Cl.$^7$ ................................. C08G 77/20
(52) U.S. Cl. ..................... 528/32; 528/12; 528/33; 528/36; 528/43; 526/279
(58) Field of Search ............. 623/6.11; 528/32, 528/12, 33, 36, 43; 526/279

(56) References Cited

U.S. PATENT DOCUMENTS

| | | |
|---|---|---|
| 4,042,613 A | 8/1977 | Takamizawa et al. |
| 4,348,454 A | 9/1982 | Eckberg |
| 4,423,195 A | 12/1983 | Covington |
| 4,675,346 A * | 6/1987 | Lin et al. |
| 4,778,862 A | 10/1988 | Woo et al. |
| 5,224,957 A | 7/1993 | Gasser et al. |
| 5,321,108 A | 6/1994 | Kunzler et al. |
| 5,391,590 A | 2/1995 | Gerace et al. |
| 5,411,553 A | 5/1995 | Gerace et al. |

FOREIGN PATENT DOCUMENTS

| | | |
|---|---|---|
| EP | 0094153 | 11/1983 |
| EP | 0414219 | 2/1991 |
| EP | 0578087 | 1/1994 |
| JP | 91-257420 | 11/1991 |
| JP | 92-159319 | 6/1992 |
| JP | 93-164995 | 8/1993 |
| WO | WO 9947185 | 9/1999 |

OTHER PUBLICATIONS

Hettlich et al, *German J. Ophthalmol.*, 1:346–349 (1992).
Haefliger et al, *Journal of Refractive & Corneal Surgery*, 10:550–555 (1994).
CAPLUS, No. 1992:201158, document No. 116:201158 & JP, A2, 03257420, 19911115.
CAPLUS, No. 1993:588650, document No. 119:188650 & JP, A2,05164995, 19930629.
CAPLUS, No. 1993:27515, document No. 118:27515 & JP, A2, 04159319, 19920602.

* cited by examiner

*Primary Examiner*—Kuo-Liang Peng
(74) *Attorney, Agent, or Firm*—Dinsmore & Shohl LLP

(57) ABSTRACT

The present invention relates to photocurable siloxane polymers having functional acryl groups, useful in the preparation of intraocular lenses (IOLs). The polymers are siloxane copolymers, wherein the siloxane can be selected from the group consisting of diphenyl siloxane, phenylalkyl siloxane, dialkyl siloxane, and trifluoroalkyl alkyl siloxane. The invention also relates to methods for producing the said siloxane polymers, as well as to producing accommodating lenses in vivo, which means that the lens is formed in the capsular bag of the eye.

16 Claims, No Drawings

PHOTOCURABLE SILOXANE POLYMERS

RELATED APPLICATIONS

The present application is a divisional of U.S. application Ser. No. 09/416,773 filed Oct. 13, 1999, now U.S. Pat. No. 6,399,734, which claims priority under 35 U.S.C. §119 of U.S. application Serial No. 60/105,580, filed Oct. 26, 1998.

FIELD OF INVENTION

The present invention relates to photocurable polysiloxanes polymers (silicones) having functional acryl groups, useful in the preparation of intraocular lenses (IOLs). The invention also relates to methods for producing elastomers comprising the said polymers, as well as to methods for producing accommodating lenses in vivo, which means that the lens is formed in the capsular bag of the eye.

BACKGROUND OF THE INVENTION

Implantation of an intraocular lens (IOL) following the extraction of a cataract is now a standard ophthalmic procedure. The conventional IOL used to replace the natural lens is a fixed focus lens manufactured from a rigid plastic such as poly(methylmethacrylate), PMMA, or from an elastomer, such as silicone. The implantation of such a lens usually necessitates the patient using spectacular correction for reading. To overcome this limitation of the conventional IOL, increasing attention has been given to bifocal and multizonal lenses.

The technique of cataract explantation and lens replacement for an accommodating IOL, an accommodating capsular lens, ACL, involves the metered injection of a low viscosity liquid, through a small incision ($\approx$1 mm diameter), into the capsular bag, followed by its polymerization under forming pressure to create a lens of the required shape, using the form of the capsular bag as the mold. To reproduce the optical performance of the natural lens, the replacement lens will require a refractive index close to 1.41. To respond to the accommodating forces of the eye, the compression modulus of IOL should be comparable to that of the natural lens which is in the range of about 1 to 5 kPa. To design materials which balance the conflicting material's requirements of the ACL requires the design of unique systems. These considerations have led a number of researchers to propose and to study the development of an ACL. An accommodative re-fill lens is an IOL formed by filling the capsular bag with the precursors of an elastomer, and causing, or allowing, the elastomer to set in the form of the natural lens. Thin-walled inflatable balloons, of silicone rubber, have also been developed which can be inserted into the capsular bag and filled with the desired system.

Most researchers of the development of the accommodative re-fill lens have used silicone-derived systems for filling the capsular bag, either in the form of silicone oils or LTV (low temperature vulcanizing) silicone elastomers. Such systems suffer from disadvantages in the context of re-fill lens formation, the dimethyl silicones have a restricted refractive index (1.40), LTVs cure slowly, up to 12 hours may be needed to complete their setting and their slow setting may result in material loss from the capsular bag through the surgical incision, further, the high viscosities of some silicone oils and intermediates make their air-bubble free injection very difficult.

Injectable formulations of polysiloxanes for making an IOL directly in the capsular bag of the human eye have been suggested in U.S. Pat. Nos. 5,278,258, 5,391,590 ('590) and U.S. Pat. No. 5,411,553 to Gerace et al as well as in U.S. Pat. No. 5,116,369 (Kushibiki et al) These patents describe mixtures of a vinyl-containing polyorganosiloxane, an organosilicone comprising hydride groups and a platinum group metal catalyst which are capable of being cured at ambient body temperature to an IOL inside the capsular bag of the eye. These compositions suffer from the general drawback of low temperature curing in that the curing process is difficult to control for the surgeon. The use of silicone fluids, demonstrating the principle of a silicone-based ACL, has been reported by Haefliger, E. and Parel, J-M. (1994) J. Refractive and Corneal Surgery 10, 550–555, but the gain in accommodation declined, probably because the system was not crosslinked.

Subsequently, the difficulties of introducing a thermally curing silicone into the capsular bag have been demonstrated. A major disadvantage of the use of a thermally curable system, such as one based on Pt-cured vinyl addition, for the "mold-in-the-bag" approach is understood from a consideration of the three characteristic phases of network formation, viz. (a) pre-gelation; (b) gelation; and (c) curing. A lens can only be molded successfully in the pre-gelation phase, and once the system has passed into its gelation phase it cannot be molded with precision. This is because the gel (polymer of infinite molecular weight) which is formed at and after the gel point has an elastic memory, and so, regardless of the forming conditions, it will always revert to its original shape with time. When molding an IOL, or ACL, this recovery process becomes evident as surface defects. such as ripples or wrinkles, which cause serious impairment of lens quality. When molding lenses from silicone systems, involving thermally induced polymerization, outside the body this phenomenon is easily regulated by adjusting the process variables of catalyst type and concentration, time, temperature and pressure. Molding an ACL within the eye during surgery imposes severe restrictions on the choice of these process variables, the molding temperature is body temperature, the molding time is the minimum compatible with the required residence time for any given patient upon the operating table, that is to say that ideally it must be variable to meet the exigencies of the surgical demands of both the ophthalmologist and the patient. In general terms, in a thermally cured silicone system, such as those based on Pt-catalysts, the durations of the pre-gelation and cure phases are coupled, a system with a short cure time has a short pre-gelation time. It is generally regarded as complicated to lengthen the pre-gelation time without lengthening the cure time.

To comply with the difficulties of controlling the thermally induced curing it would be desirable to provide systems wherein the curing is command set by the surgeon. For this purpose photocurable (i.e. photopolymerization) compositions have been contemplated. EP 0414219 describes an injectable system in which the liquid composition comprises a difunctional acrylate and/or methacrylate ester and a photoinitiator activated by light of 400–500 nm wavelength. Hettlich et al. (German J. Ophthalmol. vol. 1, 346–349, 1992) was amongst the first to propose the use of photopolymerization of a monomer system as an alternative approach to setting the material within the capsular bag. He pointed to the clinical success of blue light photocurable resins for dental applications and explored the use of such systems as injectable materials for filling capsular bags from the eyes of cadaver pigs and live rabbits. However, the systems used by Hettlich form materials with moduli too high to allow accommodative processes. Further, the introduction of acrylic monomers into the eye would be undesirable, since they are well-known to have high physiological activity.

Compositions comprising polysiloxanes with functional acrylic end groups which are curable with UV light have earlier been disclosed for the manufacture of contact lenses. Curable acrylic silicones per se have indeed been known for a considerable time in various industrial applications, as disclosed by U.S. Pat. Nos. 4,778,862 and 4,348,454. U.S. Pat. No. 5,321,108 and the Japanese patent specifications published as 3-257420, 4-159319 and 5-164995 disclose compositions of acryl-terminated polysiloxanes suitable for contact lens production. However, the compositions for making contact lenses are unsuitable for intraocular lens production directly inside the human eye, wherein specific considerations to the polysiloxanes must be taken in order to perfect an injectable lens forming material.

Consequently, there is a need for photocurable polymers and injectable compositions thereof which are adapted to be included in a composition suitable for injection into the capsular bag of the human eye. The present invention aims to perfect such polymers and compositions including them, so they meet the necessary requirements for injectable lens materials

DESCRIPTION OF THE INVENTION

It is an object of the present invention to provide photocurable polysiloxane copolymers which can be polymerized to intraocular lenses in the presence of visible light, in particular blue light.

It is a particularly important object to provide such polysiloxanes which are adapted for injection directly into the capsular sac of the human eye directly in connection to that the defect natural crystalline lens has been surgically removed.

It is another important object of the invention to provide compositions of said polysiloxanes together with a photoinitiator and further complementary additives necessary for forming the solid elastomer lens by final curing in the capsular sac.

In a general aspect the present invention relates to an polysiloxane copolymer having functional acryl groups which are capable of being photopolymerized into a solid intraocular lens with a specific gravity greater than about 1.0 and with a refractive index suitable for restoring the refractive power of the natural crystalline lens. For this purpose, the polysiloxane copolymer has siloxane monomer units are selected among substituted or unsubstituted arylsiloxanes, arylalkylsiloxanes, alkyl(alkyl)siloxanes of the general formula —$R_aR_bSiO$—. In order to accomplish suitably high refractive indices of the polysiloxane copolymer, it is preferable that one siloxane monomer unit is an arylsiloxane or an arylakylsiloxane, more preferably diphenyl siloxane or phenylmethylsiloxane. It is also highly preferred that said substitutions are fluorosubstitutions, in particular it is preferred that one siloxane monomer unit incorporates a fluroalkyl group, more preferably one siloxane monomer is fluoroalkyl(alkyl)siloxane. According to a preferred aspect, the amount of fluoroalkyl(alkyl)siloxane units exceeds about 4 mol %. This enables a special advantage of the inventive polysiloxanes by providing them with higher specific gravity than conventional polysiloxanes reported in ophthalmic use.

Functional acryl groups are defined herein by that at the polysiloxane molecules have functional groups attached thereto including an acryl group moiety, so as to become acryl-bearing, by acryl attachment to the siloxane monomers of the polysiloxane backbone, its terminal ends, or both. The acryl groups in said functional groups can be linked to the silicone atoms by spacers. Examples of functional acryl groups include acrylamidopropyl, methacrylamidopropyl, acryloxyhexyl and methacryloxyhexyl. Preferably, the functional acryl groups are attached to the terminal ends of polysiloxane molecules, as exemplified by acrylamidopropyl-, methacrylamidopropyl-, acryloxyhexyl- and methacryloxyhexyl-terminated polysiloxanes. Those skilled in the art can consider numerous such alternatives which maintain the basic function of having an acryl group for subsequent crosslinking/polymerization of the polysiloxane molecules into larger network together with a photoinitiator. In the same manner it is also to be understood that the meaning of acryl group should include acryl or substituted acryl, such as methacryl, moieties attached through a variety of linkages including ester, amide and urethane linkages, or functional analogues of acryl capable of undergoing crosslinking reactions with a photoinitiator.

In a further aspect, the invention relates to a process for production of polysiloxane copolymer having functional acryl groups, as described above. Such a process is generally described in the Examples below and the skilled person will be able to make suitable modifications in order to prepare other copolymers within the scope of the invention.

The polysiloxane copolymers having functional acryl groups according to the present invention should preferably have a refractive index above about 1.39 in order to restore the refractive index of the natural lens which has a refractive index of about 1.41. It is an important aspect of the present invention to be able to control the refractive index of polysiloxanes by selection of its siloxane monomer composition and thereby the refractive outcome of the final implanted lens. It is to be understood that refractive indices can be up to about 1.60 is within the context of the present application if this is required for a specific optical application. This further considered in the co-pending International Patent Application with even filing date claiming priority from U.S. patent application Ser. No. 09/170,160 which hereby is incorporated as a reference.

According to a preferred aspect of the present invention, the polysiloxane copolymer having functional acryl groups can be obtained from a copolymer having the general formula:

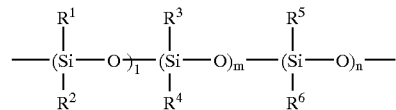

wherein $R^1$ and $R^2$ are independently $C_1$–$C_6$ alkyl; $R^3$ is phenyl; $R^4$ is phenyl or $C_1$–$C_6$ alkyl; $R^5$ is $CF_3(CH_2)_x$ wherein x is 1–5; $R^6$ is $C_1$–$C_6$ alkyl or fluoroalkyl; 1 is in the molar fraction range of 0 to 0.95; mis in the molar fraction range of 0 to 0.7; and n is in the molar fraction range of 0 to 0.65, the copolymer having functional acryl groups at the terminal ends thereof. In one embodiment, 1 is in the molar fraction range of from greater than 0 to 0.95. In a further embodiment, m is in the molar fraction range of from greater than 0 to 0.7; and n is in the molar fraction range of greater than 0 to 0.65.

It is preferred that $R^1$ is methyl, that $R^2$ is methyl, $R^4$ is phenyl, that x is 2, either independently, or in combination.

Preferably according to these alternatives $R^6$ is methyl. According to one embodiment, the polysiloxane is a copolymer of diphenyl or phenylalkyl siloxane and dialkyl siloxane with terminal acryl groups. According to further embodiments, the polysiloxane is a copolymer of diphenyl or phenylalkyl siloxane and trifluoroalkyl(alkyl)siloxane, or a terpolymer or higher order polymer of diphenyl and/or phenylalkyl siloxane, dialkyl siloxane and trifluoroalkyl alkyl siloxane. According to a specific preferred embodiment, polysiloxane is an acryl-terminated terpolymer of dimethyl siloxane, diphenyl siloxane or phenylmethyl siloxane and 3,3,3-trifluoropropylmethyl siloxane. Preferably, said polysiloxanes comprise at least about 4 mol % of trifluoropropylmethyl siloxane and 1 to 50 mol % of diphenylsiloxane and/or phenylmethylsiloxane. More preferably said polysiloxanes comprise about 4 to 65 mol % trifluoropropylmethyl siloxane, 1 to 50 mol % of diphenylsiloxane and dimethylsiloxane monomer units. One suitable acryl-terminated polysiloxane composition comprises about 28 mol % trifluoropropylmethyl siloxane, about 4 mol % diphenyl siloxane and dimethyl siloxane monomer units.

The invention also relates to an injectable lens material having a suitable viscosity to be injected through standard cannula with an 18 Gauge needle or finer. For this purpose the material should preferably have a viscosity lower than about 60 000 cSt or below about 8000 cSt for being readily injectable through a 21 Gauge needle. The injectable lens material is composition of at least one type of polysiloxanes according to any of the definitions above, a photoinitiator, optionally a crosslinking agent, which in itself can be siloxane oligomer or polymer having functional acryl groups and further physiologically or ophthalmologically acceptable additives necessary for producing a lens. The composition is preferably formed as fluid mixture from separately stored constituents which are protected from reactivity during storage. This type of kits or multi-chamber cartridges with mixing equipment and their operation are well known in the art of pharmaceuticals or silicone products and will not be discussed here in further detail. To reduce physiological hazards, only acryl-substituted siloxane polymers are introduced into the capsular bag, together with medically acceptable photoinitiators activated in the visible range, including blue light activated types derived from acyl phosphine oxides and bisacylphosphine oxides, in low molecular weight and high molecular weight (polymeric) forms, and titianocene-photoinitiators. Important characteristics of these photoinitiators for injectable lens applications are that they initiate the photopolymerization of acryl groups when exposed to visible light, preferably blue light and that they are "photobleaching" and so they are efficient as photoinitiators for the rapid curing of thick sections (1–5 mm). Suitable photoinitiators for injectable lens forming compositions are also discussed in WO 99/47185 and in the Swedish Patent Application No. 9900935-9 which both are incorporated herein as references. For the embodiment discussed in said Swedish Patent Application No. 9900935-9, wherein the photoinitiator is a conjugate of a photoactive groups and a macromolecule capable of participating in a crosslinking reaction with acryl-terminated polysiloxanes, the macromolecule in such a photocrosslinker should be a polysiloxane compatible with said first polysiloxanes. The injectable lens material composition can also comprise said polysiloxanes having functional acryl groups, a photoinitiator according to above and a separate crosslinking agent. Suitable crosslinking agents can be found among di- or tri- and higher order acrylates, methacrylates, acrylamides, methacrylamides including siloxane oligomers and polymers having functional acryl groups. Short molecule crosslinkers are exemplified by hexanediol acrylate, tripropyleneglycol diacrylate. Polymeric crosslinkers, suitable for injectable IOL applications are exemplified by copolymers or higher order polymers incorporating (methacryloxypropyl)methylsiloxane units.

Further, the invention relates to a method of producing an elastomer, preferably an intraocular lens, by preparing polysiloxane copolymers with functional acryl groups as previously defined, mixing said copolymers with a photoinitiator and optionally a crosslinking agent, injecting said mixture into a lens forming mold, irradiating the injected mixture with light so as to form the solid elastomer. Most preferably, according to the present invention the mixture is injected into the human eye to form an implant to replace the natural lens, but the method is also conceivable in non-surgical processes, such as conventional lens manufacturing with injection molding.

A method of in vivo production of an intraocular lens, will comprise the steps of preparing an polysiloxane copolymer having functional acryl groups according to the invention; mixing said copolymer and a photoinitiator, preferably a medically acceptable blue light photoinitiator, to a composition; injecting said composition comprising said copolymer and photoinitiator into the capsular bag of the eye; and initiating a polymerization reaction to create a lens in the capsular bag.

The invention also relates to an elastomer manufactured by the process described above. Preferably, such an elastomer is in the form of an optical lens, which preferably has a refractive index between 1.39 and 1.46, or, more preferably, close to 1.41. To obtain optical lenses having the desired refractive index, the proportions between the copolymer precursors should preferably be close to the proportions demonstrated in the Examples given below. However, as mentioned above it is possible to obtain higher lenses with higher refractive indices up to about 1.60 according to the present invention if this is necessary to obtain specific refraction values in certain clinical applications. Further, by employing the polysiloxanes with functional acryl groups, the injectable material and the methods of the present invention lenses with a compression modulus suitable to undergo accommodation by the forces of the eye can be obtained. Typically, lenses having a modulus below about 55 kPa and in the range of about 20 to 50 kPa can readily be obtained by employing the present invention which are functionally accommodatable by the human eye. Optionally, the elastomer according to the invention can also comprise an UV absorbing compound or other conventional additives known to those skilled in the art.

The invention further relates to a medicinal kit consisting of part (a) comprising polysiloxane copolymers having functional acryl groups according to the invention; and a part (b) comprising a clinically acceptable photoinitiator. The combination gives liquid silicone polymers of controlled photo-reactivity that can be "command set" by photopolymerization, upon exposure to blue light. The specification of this photo-crosslinkable system derives from an interplay of the viscosity and the injection density of the initial polymer solution, as well as the refractive index, modulus and compressive characteristics of the photocured gel.

A special advantage of the materials of this invention is that the incorporation of a fluoroalkyl siloxane enables materials of higher specific gravity to be produced than has previously been reported in silicones for ophthalmic use. Polydimethylsiloxane (PDMS), having refractive index 1.403 and specific gravity ca. 0.97–0.98, has been reported as a material for an injectable IOL. However, whilst the refractive index of PDMS approximately matches that of the human lens, the lower specific gravity of PDMS can present considerable difficulty for the surgeon as PDMS floats in aqueous solution. This makes complete filling of the capsular bag with exclusion of aqueous fluid difficult in the case of direct injection Copolymers of dimethyl and diphenyl siloxanes have higher specific gravity than PDMS. However, the diphenyl content of the copolymers increases the refractive index, thus, for example, it is not possible to have a dimethyl-diphenyl copolymer with a specific gravity greater than 1.0 and a refractive index of less than approximately 1.44. Materials of the present invention, being copolymers, terpolymers or higher order polymers, incorporating fluoroalkyl siloxane units, enable silicones of specific gravity greater than 1.0 to be produced over a wider range of refractive index than has previously been reported.

DETAILED AND EXEMPLIFYING PART OF THE DESCRIPTION

The following examples aim to illustrate methods of preparing polysiloxanes having functional acryl groups and their subsequent photopolymerization. The preparation of acryl terminated siloxanes in general has been well reported (see Thomas, D. R.: p.610 in "Siloxane Polymers" (Clarson, S. J. and Semlyen. J. A., eds.) New Jersey. 1993) and the examples given below are those preferred of the many routes. The preparation of acrylic terminated terpolymers of dimethylsiloxane/diphenyl-siloxane/methyl,3,3,3-trifluoropropylsiloxane have not been reported.

EXAMPLE 1
Preparation of aminopropyl-terminated poly(dimethyl-co-diphenyl)siloxane Distilled octamethylcyclotetrasiloxane (27.5 g, 92.9 mmol, 82.1 mol %), recrystallised octaphenylcyclotetrasiloxane (16.1 g, 20.3 mmol, 17.9 mol %), and 1,3-bis(3-aminopropyl)tetramethyldisiloxane (0.641 g, 2.73 mmol) were carefully charged to a three-necked flask. The flask was equipped with a mechanical stirrer, purged with nitrogen then potassium hydroxide (80 mg) catalyst was added. The reaction mixture was heated to 160° C. and stirred 24 h. The catalyst was then neutralized by the addition of 0.24 g of 36% HCl aq. as a solution in 3 ml ethanol, with stirring, and the mixture cooled to 25° C. The clear colourless silicone fluid obtained was diluted with 100 ml diethyl ether and transferred to a separating funnel. After extracting twice with 100 ml portions water to remove the catalyst, the solution was dried with magnesium sulphate. The product was filtered, and the solvent evaporated. The clear viscous fluid was heated to 110° C. in vacuo (0.2 torr) to remove residual solvent and volatile products. Yield was 42.05 g (95%).

EXAMPLE 2
Preparation of aminopropyl-terminated poly(dimethyl-co-diphenyl-co-trifluoropropylmethyl)siloxane Distilled octamethylcyclotetrasiloxane (83.56 g, 0.282 mol), octaphenylcyclotetrasiloxane (11.77 g, 0.0148 mol), and distilled 3,3,3-trifluoropropylmethylcyclotrisiloxane (27.56 g, 0.0588 mol) were weighed to a flask and dried under vacuum at 80° C. for 30 minutes. The flask was purged with nitrogen and 1,3-bis(3-aminopropyl)tetramethyldisiloxane (3.107 g, 0.0125 mol) end-capper was injected via a septum. Potassium silanolate initiator (0.055 g) was added, the temperature raised to 160° C., and mixture heated and stirred for 36 hours. The clear colourless product was allowed to cool, diluted with 57 ml chloroform and washed: three times with 88 ml portions water; twice with 88 ml portions methanol; then the product was diluted with 44 ml tetrahydrofuran and washed twice more with 88 ml portions methanol. Solvent and volatiles were stripped by heating at 100° C. under vacuum (pressure falling to <1 mbar). The product obtained was clear and colourless. Yield: 90.72 g (71.9%). Analysis showed refractive index at 25° C.: 1.417 (theory: 1.417), density: 1.048 g/ml (theory: 1.059), and molecular weights by gel permeation chromatography (GPC) with polystyrene standards: Mn 25,900 Mw 71,800. (The high polydispersity shown in the GPC results suggest reaction was still not fully complete after 36–40 hours; this problem could be improved by use of a bisaminosiloxane oligomeric end-capper). Polymer unit ratios by H-NMR, 500 MHz, dimethyl/diphenyl/trifluoropropyl were: 0.816/0.047/0.137 (starting monomer ratios were: 0.792/0.042/0.165). Amino-terminated polysiloxanes, prepared by this route were used as starting material for preparing acrylamidoalkyl- and methacrylamidoalkyl-terminated silicones.

EXAMPLE 3
Preparation of aminopropyl-terminated poly(dimethyl-co-diphenyl-co-trifluoropropylmethyl)siloxane Example 2 was repeated with different monomer combinations: octamethylcyclotetrasiloxane (84.54 g, 0.285 mol), octaphenylcyclotetrasiloxane (16.15 g, 0.0204 mol), and distilled 3,3,3-trifluoropropylmethylcyclotrisiloxane (21.20 g, 0.0452 mol), 1,3-bis(3-aminopropyl)tetramethyldisiloxane (3.118 g, 0.0125 mol potassium silanolate initiator (0.056 g). Yield was 88.44 g (70.6%). Analysis showed refractive index at 25° C.: 1.425 (theory: 1.426), density: 1.046 g/ml (theory: 1.051), and molecular weights: Mn 19,600 Mw 69,400. Polymer unit ratios by H-NMR, dimethyl/diphenyl/trifluoropropyl were: 0.832/0.065/0.104 (starting monomer ratios were: 0.813/0.058/0.129).

EXAMPLE 4
Preparation of aminopropyl-terminated poly(dimethyl-co-diphenyl-co-trifluoropropylmethyl)siloxane Example 2 was repeated with different monomer combinations: octamethylcyclotetrasiloxane (62.66 g, 0.211 mol), octaphenylcyclotetrasiloxane (34.38 g, 0.0433 mol) and distilled 3,3,3-trifluoropropylmethylcyclotrisiloxane (24.87 g, 0.0531 mol), 1,3-bis(3-aminopropyl)tetramethyldisiloxane (3.327 g, 0.0134 mol) potassium silanolate initiator (0.055 g). Yield was 77.07 g (61.0%). Analysis showed refractive index at 25° C.: 1.455 (theory: 1.456), density: 1.083 g/ml (theory: 1.090). Polymer unit ratios by NMR, dimethyl/diphenyl/trifluoropropyl were: 0.696/0.161/0.143 (starting monomer ratios were: 0.686/0.141/0.173).

EXAMPLE 5
Preparation of hydroxyhexyl-terminated poly(dimethyl-co-diphenyl)siloxane Distilled octamethylcyclotetrasiloxane (27.54 g, 92.9 mmol, 82.1 mol %) and recrystallised octaphenylcyclotetrasiloxane (16.11 g, 20.3 mmol, 17.9 mol %) were carefully charged into a three-necked flask. The reactor was equipped with a mechanical stirrer; purged with nitrogen, and tetramethylammonium hydroxide (60 mg) catalyst added. The reaction mixture was heated to 110° C. with stirring for 2 hours, becoming viscous, followed by 3 hours heating at 160° C. to decompose the tetramethylammonium hydroxide catalyst. 1,3-Bis(6-hydroxyhexyl)tetramethyldisil (0.916 g, 2.74 mmol) end-capper (calculated Mn: 16'000) and 1 ml trifluoromethanesulfonic acid catalyst were added and the mixture stirred 6 hours at 60° C. The resulting viscous fluid was diluted with 100 ml tetrahydrofuran and vigorously stirred with 5% sodium hydroxide at 25° C. in order to deliberate the hydroxyl end group. The saponification process was monitored by IR spectroscopy, samples being withdrawn from time to time. After 12 hours the process was 95% complete by IR. (Longer time risked cleavage of the end group by a base catalysed process). The mixture was transferred to a separating funnel, the two phases separated, and the organic layer washed with water (3×100 ml). The solution was dried with first sodium sulphate then magnesium sulphate, and filtered. After initial evaporation of the solvent, the clear viscous fluid was heated to 110° C. in vacuo (0.2 torr) to remove residual solvent and some volatile products, affording a colourless viscous fluid end product. Yield. 32.81 g (73.6%). The copolymer unit composition by 1H-NMR (400MHz, CDCl$_3$) was 17.9 mol % diphenyl-units before vacuum treatment, and 19.1 mol % after. Hydroxy-terminated polysiloxane, prepared by this route can be used as starting material for preparing acryloxy- and methacryloxy-terminated silicones.

EXAMPLE 6
Preparation of acrylamidopropyl-terminated poly(dimethyl-co-diphenyl)siloxane Aminopropyl-terminated poly(dimethyl-co-diphenyl) siloxane (40 g, 4.25 meq) as prepared in Example 1, was dissolved in 100 ml dry dichloromethane and 2 g calcium hydride was added in three portions. The mixture was cooled to 0. degree. C. and acryloyl chloride (640 mg, 570 μl, 7.0 mmol) was added. The suspension was stirred over night, and the calcium hydride and calcium chloride were removed by filtration. The filtrate was washed with water (100 ml) then dried with sodium sulphate (later magnesium sulphate). Solvent was evaporated, first at 20 torr then at 0.2 torr, at room temperature. This sample was used for rheology measurements and injection into a pig cadaver eye. However, subsequent GPC analysis showed cyclic impurities to be present, so further washing was performed. A portion of sample. 20.35 g, as diluted with 20 ml toluene and the solution precipitated to stirred methanol. The silicone was allowed to separate, and again diluted with toluene and precipitated to methanol, as before. The silicone was transferred to a flask, and the solvent removed under vacuum (to 1.5 mbar) with gentle heating in stages. This sample is referred to as Example 6 'post-washing'. Acrylamidopropyl end groups by NMR (500MHz) gave Mn 21,000 (0.095 meq/g).

EXAMPLE 7
Preparation of acrylamidopropyl-terminated poly(dimethyl-co-diphenyl-co-trifluoropropylmethyl)siloxane Aminopropyl-terminated terpolymer of Example 2 (15.02 g, 1.50 mmol based on theoretic Mn 10,000) was weighed to a dried flask, and nitrogen flow applied. Dried dichloromethane (40 ml) was added, followed by calcium hydride (1 g), added in small portions. The flask was cooled in ice-water until the temperature of the contents was 0° C., then distilled acryloyl chloride (0.380 g, 4.2 mmol) was added via a septum. The reaction was stirred for 30 minutes at 0. degree. C. then the ice was removed and the mixture allowed to warm to ambient over 3.5 hours. The turbid mixture was filtered under reduced pressure, with dichloromethane rinsing, to remove CaH.sub.7 and CaCl.sub.2. The solution was washed with 50 ml water dried over magnesium sulphate, and the solvent removed under vacuum, initially on a rotary evaporator then on a bath at 50° C. with pressure to <1 mbar. Yield: 13.28 g (87%). The H-NMR spectrum showed unattached acrylic reagent to be present, so the product was re-precipitated twice, each time with dilution in 20 ml dichloromethane and precipitation to 200 ml stirred methanol. Solvent was then removed under vacuum as before, giving a clear colourless product. Yield: 6.43 g (42%). Analysis by 500 MHz H-NMR showed no unattached acrylic reagent and gave unit ratios dimethylsiloxane/diphenyl-/trifluoropropyl-/acrylamide of 0.817/0.0468/0.131/0.0102 implying Mn 17,800. Conversion of the amino groups appeared quantitative.

EXAMPLE 8
Preparation of methacrylamidopropyl-terminated poly (dimethyl-co-diphenyl-co-trifluoropropylmethyl)siloxane Example 6 was repeated using methacryloyl chloride as modification reagent. Aminopropyl-terminated terpolymer of Example 3 (15.11 g, 1.50 mmol based on theoretic Mn 10,000) was reacted with distilled methacryloyl chloride (0.439 g, 4.2 mmol), other reagents and the method being the identical. The final yield was 10.06 g (66%). Analysis by 500 MHz H-NMR gave unit ratios dimethylsiloxane/diphenyl-/trifluoropropyl-/acrylamide of 0.827/0.064/0.099/0.0105 implying Mn 17,200. Again conversion of the amino groups appeared quantitative.

EXAMPLE 9
Rheological Measurements of Photocured Materials

Silicones prepared as above (Examples 6, 7, & 8) were photocured by blue light and colourless glass-clear elastomers were produced, and their moduli measured. Comparison has been made with elastomers from commercially available photocurable silicones, and measurements made both with and without an additional crosslinker. Compositions for rheological testing were prepared in ca.3 g batches under subdued light, with weighing to ±0.01 mg. To ensure dissolution in the silicone, the photoinitiator was first dissolved in 1–1.5 ml dichloromethane and this solution was stirred for 3 minutes with the silicone, then the solvent removed by vacuum desiccation to constant weight at room temperature (typically ca.30 minutes with pressure to 0.3 mbar).Disks for analysis were cast in a Teflon mould (diameter 25 mm, depth 1.0 mm) which was filled with the composition and then covered with a microscope slide, so as to give a smooth contact surface over the entire diameter of the mould, and the composition was then cured using blue light. (Source was a Vivadent Heliolux DLX dental gun, emitting 400–525 nm, placed 22 mm above the mould, at which distance the light intensity was 13–14 m W/cm$^2$). Measurements of the shear (storage) modulus were then performed on the disks using a Rheometrics RDA 2 rheometer at 35° C. A photoinitiator active in the blue light region was used: bis(2,4,6-trimethylbenzoyl)phenylphosphine oxide (Ciba Irgacure 819). The photoinitiator concentration used was 0.20% ww in all the examples quoted herein. For comparison, studies were also made of commercial photocuring silicones: methacryloxypropyl-terminated polydimethylsiloxane (Gelest-ABCR DMS-R31), Mn 24,800 by NMR, 0.081 meq/g methacryloxy; and acryloxy-terminated polydimethylsiloxane (Gelest-ABCR DMS-U22), Mn 768 by NMR, 2.60 meq/g acryloxy, which because of its low Mn was here employed as a crosslinker. An alkyl crosslinker, tripropyleneglycol diacrylate, TPGDA (Genomer 1230), was also used.

| Example | Silicone polymer | Crosslinker type | % ww | Shear modulus G'/kPa at 35° C. |
|---|---|---|---|---|
| 9(a) | Methacryloxypropyl-terminated polydimethylsiloxane ABCR DMS-R31 | — | — | 21.0 |
| 9(b) | Methacryloxypropyl-terminated polydimethylsiloxane ABCR DMS-R31 | TPGDA | 0.57 | 46.1 |
| 9(c) | Methacryloxypropyl-terminated polydimethylsiloxane ABCR DMS-R31 | " | 1.14 | 48.1 |
| 9(d) | Methacryloxypropyl-terminated polydimethylsiloxane ABCR DMS-R31 | Acryloxy-terminated polydimethylsiloxane ABCR DMS-U22 | 0.76 | 45.3 |
| 9(e) | Acrylamidopropyl-terminated poly(dimethyl-co-diphenyl)siloxane (Example 6) | — | — | 46.5 |
| 9(f) | Acrylamidopropyl-terminated poly(dimethyl-co-diphenyl)siloxane (Example 6) | TPGDA | 1.05 | 51.6 |
| 9(g) | Acrylamidopropyl-terminated poly(dimethyl-co-diphenyl)siloxane (Example 6: post washing) | — | — | 52.7 |
| 9(h) | Acrylamidopropyl-terminated poly(dimethyl-co-diphenyl-co-trifluoropropyl)siloxane (Example 7) | — | — | 55.8 |
| 9(i) | Acrylamidopropyl-terminated poly(dimethyl-co-diphenyl-co-trifluoropropyl)siloxane (Example 8) | — | — | 65.3 |

EXAMPLE 10
Preparation of a Photocured Intraocular Lens

Acrylamidopropyl-terminated poly(dimethyl-co-diphenyl)siloxane (Example 2) containing photoinitiator (Irgacure 819, 0.20% ww) and crosslinker (TPGDA, 0.57%) was prepared as per Example 9(b). A fresh pig cadaver eye was prepared, with small aperture incision into the capsular bag and removal of the crystalline lens. The silicone composition was injected into the capsular bag via a 21 gauge cannula, so as to refill the bag and give appropriate curvature. The silicone was cured by blue light from a Vivadent Heliolux DLX dental gun placed 0.5–1.0 cm in front of the cornea, and the lens was extracted to enable examination. The clear colourless tack-free lens had anterior radius 12.0±0.5 mm, posterior radius 5.19±0.1 mm thickness 5.06±0.02 mm, diameter 8.9±0.1 mm. Its power in air was 108±2 diopter, and focal length 9.2±0.2 mm (in water: 27.1±0.5 diopter, and focal length 37.0±0.7 mm).

EXAMPLE 11

EXAMPLE 11.1
(a) Preparation of dimethylsiloxane/diphenylsiloxane/methyl,3,3,3-trifluoropropylsiloxane terpolymers Octamethylcyclotetrasiloxane (D4) (6.0 g, 20 mmoles), octaphenyl-cyclotetrasiloxane (DPh4) (1.7 g, 2 mmoles) and trimethyl- tris(3,3,3-trifluoropropyl)cyclotrisiloxane (23% cis and 77% trans, F3) (7.3 g, 16 mmoles) were added to bis(3-aminopropyl) dimethyldisiloxane (0.15 to 0.3 g), and purged with argon. The temperature was raised to +120° C. and bis(tetramethylammonium)-polydimethylsiloxanolate catalyst (0.01 g) added, and the reaction heated for 2–3 h at +120° C. and 3 h at +160° C. Upon cooling to ambient temperature the polymer was dissolved in tetrahydrofuran and precipitated and washed with methanol, centrifuged, and dried in vacuo. The resulting polysiloxane had a number average molecular weight >10 kDa, a refractive index >1.40 and a density >1.10.

(b) Introduction of Acrylic Groups

A dimethylsiloxane/diphenylsiloxane/methyl,3,3,3-trifluoropropylsiloxane terpolymer, from type (a) preparations above, (4.0 g, 0.04 mmoles) was dissolved in methylene dichloride to yield a 10–20 weight % solution, an excess of finely divided CaH added and the resulting suspension cooled to 0° C. and purged with argon. Acryloyl chloride (0.15 g, 0.14 mmoles) dissolve in methylene dichloride (3 ml) was added dropwise, with stirring and cooling to ensure that the temperature of reaction did not rise above 0° C. After complete addition of the acryloyl chloride the solution was stirred for 4 h and allowed to warm to ambient temperature. The suspension was filtered and the filtrate neutralized with $NaHCO_3$, washed with water, dried over anhydrous $MgSO_4$, and evaporated in vacuo The resulting acrylic-terminated terpolymer was stabilized by the addition of 1–3 ppm of hydroquinone. The resulting polysiloxane can be photopolymerized to form flexible lenses of very low modulus, by exposure to blue light whilst retained in a suitable mold, such as a cadaver pig's eye capsular bag, or a silicone balloon, or a transparent plastic mold. The photoinitiation is caused by the inclusion of e.g. 2% TMPO prior to isolation of the siloxane which was completed in the absence of blue light.

EXAMPLE 11.2
(a) Formation of Polysiloxane, Silanol-Terminated

Hexamethylcyclotrisiloxane (D3) (6.0 g, 27 mmoles), hexaphenyl-cyclotrisiloxane (DPh3) (1.7 g, 2.7 mmoles) and trimethyl-tris(3,3,3-trifluoropropyl)cyclotrisiloxane (cis and trans F3) (7.3 g, 21 mmoles) were dissolved in methylene chloride to which was added trimethylsilyl triflate (TMST)

(0.23 g) and 2,6-di-t-butylpyridine (0.15 to 0.2 g), and purged with dry argon. Terpolymerization proceeded at ambient temperature and was completed within 24 h. The polymerization proceeds by a non-terminating chain growth mechanism and so the molecular weight of the copolymers was dependent upon the ratio monomers to TMST, the reaction was terminated by the addition of an excess (over TMST) of $NaHCO_3$. The resulting terpolymer solution was washed with dilute HCl (0.2 M) and with water (3x), dried over anhydrous $MgSO_4$, and solvent and residual cyclics removed by vacuum distillation at low temperature. The siloxane terpolymer had a number average molecular weight >10 kDa, a refractive index >1.40 and a density >1.10. Instead of TMST, trifluoromethanesulphonic acid (triflic acid) and its derivatives, e.g., benzyldimethyl triflate, can be used.

(b) Preparation of Acrylic Terminated Terpolymer Silanols

The silanol terminated terpolymer of hexamethylcyclotrisiloxane (D3), hexaphenylcyclotrisiloxane (DPh3) and trimethyltris(3,3,3-trifluoropropyl) cyclotrisiloxane (cis and trans F3) was mixed with acryloxymethyldimethylacryloxysilane (prepared as described by Chu et al. in U.S. Pat. No. 5,179,134, 1993, to Loctite Corporation) in equimolar ratio, at ambient temperature. After standing for 2 h the by-product, acrylic acid was removed by vacuum stripping.

EXAMPLE 11.3

A silanol terminated dimethyldiphenylsiloxane (viscosity 2000–3000 cSt; molecular weight 35 kDa mole % diphenylsiloxane 1–2) (4.0 g, 0.12 mmoles) was dissolved in methylene chloride to yield a 15 weight solution, and an excess of finely divided CaH was added. The resulting solution was purged with argon and cooled to 0° C., when acetoxy (bisacryloethyl)methylsilane (0.15 g, 1.4 mmoles) dissolved in methylene chloride, together with an addition of 50 ppm of dibutyltin dilaurate, was added dropwise with stirring. Stirring the reaction was continued for a further 4 h and the resulting suspension was filtered. The filtrate was dried over anhydrous Mg.sub.2 SO.sub.4 and evaporated to dryness in vacuo.

EXAMPLE 12
Photopolymerization of Acryl-Terminated Polysiloxane Terpolymers

A number of visible light photoinitiators is available for initiating the acrylic photopolymerization of the acrylic-terminated D3IDPh3IF3 terpolymers described above, and these include titanocenes, such as bis(h.sup.5-cyclopentadienyl)-bis[2,6-difluoro-3-(1H-pyr-1-yl)phenyl] titanium (Til), and acylphosphine oxides, such as 2,4,6-trimethylbenzoyl-diphenylphosphite oxide (TMPO), and polymer variants such as Lucirin (a polymeric derivative of TMPO; see Angiolini, L. et al. (1995) J. Appi. Polym. Sci. 57, 519).

EXAMPLE 12.1

Acrylic-terminated D3/DPh3/F3 terpolymer and Til (0.5%) were mixed and irradiated with light from a 488 nm A-laser. The combination gelled rapidly to yield an elastomer of low modulus, a refractive index >1.40 and a density >1.10.

EXAMPLE 12.2

Acrylic-terminated D3/DPh3/F3 terpolymer and TMPO (3.0%) were mixed and irradiated with light from a blue light gun. The combination gelled rapidly (less than 3 min) to yield an elastomer of low modulus, a refractive index >1.40 and a density >1.10.

EXAMPLE 12.3

Acrylic-terminated D3/DPh3/F3 terpolymer and Lucirin (2%) were mixed and irradiated with a blue light gun. The combination gelled rapidly to yield an elastomer of low modulus, a refractive index >1.40 and a density >1.10.

What is claimed is:

1. A photopolymerizable polysiloxane copolymer having functional acryl groups at terminal ends thereof, a specific gravity greater than about 1.0, and a refractive index suitable for restoring the refractive power of the natural crystalline lens, wherein the polysiloxane copolymer has siloxane monomer units selected from the group consisting of substituted and unsubstituted arylsiloxanes, substituted and unsubstituted arylalkylsiloxanes, substituted and unsubstituted alkyl(alkyl)siloxanes, and mixtures thereof, wherein at least one of the siloxane monomer units is substituted with one or more fluorine atoms, and wherein at least one siloxane monomer unit is an arylsiloxane or an arylalkylsiloxane.

2. The polysiloxane copolymer according to claim 1, having a refractive index above about 1.39.

3. A polysiloxane copolymer according to claim 1, having a backbone of the general formula:

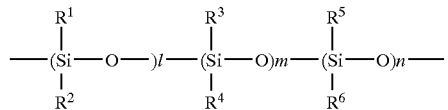

wherein $R^1$ and $R^2$ are independently $C_1$–$C_6$ alkyl; $R^3$ is phenyl; $R^4$ is phenyl or $C_1$–$C_6$ alkyl; $R^5$ is $CF_3(CH_2)_x$ wherein x is 1–5; $R^6$ is $C_1$–$C_6$ alkyl or or fluoroalkyl; 1 is in the molar fraction range of 0 to 0.95; m is in the molar fraction range of from greater than 0 to 0.7; and n is in the molar fraction range of from greater than 0 to 0.65.

4. The copolymer according to claim 3, wherein $R^1$ is methyl.

5. The copolymer according to claim 4, wherein $R^2$ is methyl.

6. The copolymer according to claim 5, wherein $R^4$ is phenyl.

7. The copolymer according to claim 3, wherein $R^4$ is phenyl.

8. The copolymer according to claim 3, wherein x is 2.

9. The copolymer according to claim 6, wherein x is 2.

10. The copolymer according to claim 3, wherein $R^6$ is 2 methyl.

11. The copolymer according to claim 9, wherein $R^6$ is methyl.

12. The copolymer according to claim 3, wherein 1 is in the molar range of from greater than 0 to 0.95.

13. The copolymer according to claim 3, wherein the copolymer is a copolymer of diphenyl siloxane or phenylalkyl siloxane units and trifluoroalkyl alkyl siloxane units.

14. The copolymer according to claim 3, wherein the copolymer is a terpolymer or higher order copolymer of diphenyl siloxane or phenylalkyl siloxane units, dialkyl siloxane units and trifluoroalkyl alkyl siloxane units.

15. The copolymer according to claim 5, wherein the copolymer is a terpolymer of dimethyl siloxane units, diphenyl siloxane units and trifluoroalkyl methyl siloxane units.

16. The copolymer according to claim 1, having a viscosity of less than about 60,000 cSt.

* * * * *

UNITED STATES PATENT AND TRADEMARK OFFICE
CERTIFICATE OF CORRECTION

PATENT NO.   : 6,737,496 B2
DATED        : May 18, 2004
INVENTOR(S)  : Kenneth A. Hodd et al.

It is certified that error appears in the above-identified patent and that said Letters Patent is hereby corrected as shown below:

Column 14,
Line 47, change "wherein $R^6$ is 2" to -- wherein $R^6$ is --.

Signed and Sealed this

Eighth Day of February, 2005

JON W. DUDAS
*Director of the United States Patent and Trademark Office*